US012558394B2

(12) United States Patent
Xiao et al.

(10) Patent No.: US 12,558,394 B2
(45) Date of Patent: Feb. 24, 2026

(54) APPLICATION OF TRADITIONAL CHINESE MEDICINE COMPOSITION TO PREPARATION OF MEDICINE FOR TREATING OR PREVENTING CORONAVIRUS INFECTION

(71) Applicant: JIANGSU KANION PHARMACEUTICAL CO., LTD., Jiangsu (CN)

(72) Inventors: Wei Xiao, Lianyungang (CN); Xiaoqian Tao, Lianyungang (CN); Xinzhuang Zhang, Lianyungang (CN); Zhenzhen Su, Lianyungang (CN); Zhipeng Ke, Lianyungang (CN); Zeyu Cao, Lianyungang (CN); Liang Cao, Lianyungang (CN); Xiaolian He, Lianyungang (CN); Xuehong Dong, Lianyungang (CN); Yanqiu Wang, Lianyungang (CN)

(73) Assignee: JIANGSU KANION PHARMACEUTICAL CO., LTD., Lianyungang (CN)

( * ) Notice: Subject to any disclaimer, the term of this patent is extended or adjusted under 35 U.S.C. 154(b) by 571 days.

(21) Appl. No.: 17/919,947

(22) PCT Filed: Mar. 11, 2021

(86) PCT No.: PCT/CN2021/080152
§ 371 (c)(1),
(2) Date: Oct. 19, 2022

(87) PCT Pub. No.: WO2021/213058
PCT Pub. Date: Oct. 28, 2021

(65) Prior Publication Data
US 2023/0158095 A1 May 25, 2023

(30) Foreign Application Priority Data
Apr. 21, 2020 (CN) .......................... 202010319195.1

(51) Int. Cl.
| | |
|---|---|
| A61K 36/78 | (2006.01) |
| A61K 36/282 | (2006.01) |
| A61K 36/355 | (2006.01) |
| A61K 36/534 | (2006.01) |
| A61K 36/65 | (2006.01) |
| A61P 31/14 | (2006.01) |

(52) U.S. Cl.
CPC ............ *A61K 36/78* (2013.01); *A61K 36/282* (2013.01); *A61K 36/355* (2013.01); *A61K 36/534* (2013.01); *A61K 36/65* (2013.01);

*A61P 31/14* (2018.01); *A61K 2236/331* (2013.01); *A61K 2236/333* (2013.01); *A61K 2236/39* (2013.01)

(58) Field of Classification Search
None
See application file for complete search history.

(56) References Cited

FOREIGN PATENT DOCUMENTS

| | | |
|---|---|---|
| CN | 102688332 A | 9/2012 |
| CN | 103675135 A | 3/2014 |
| CN | 108938803 A | 12/2018 |
| CN | 110882321 A | 3/2020 |
| CN | 111603515 A | 9/2020 |

OTHER PUBLICATIONS

English translation of the Written Opinion for PCT/CN2021/080152—mailed Jun. 15, 2021.*
"COVID-19: Prevention and risks"—https://www.canada.ca/en/public-health/services/diseases/2019-novel-coronavirus-infection/prevention-risks.html—accessed Jan. 2023.*
English translation of CN 102688332 A—2012.*
Geraghty (Viruses (2021), vol. 13, p. 667).*
"MERS-COV" https://www.who.int/health-topics/severe-acute-respiratory-syndrome#tab=tab_3—accessed Jan. 2023.*
"SARS"—https://www.who.int/health-topics/severe-acute-respiratory-syndrome#tab=tab_3—accessed Jan. 2023.*
"COVID-19 Information" website ("What You Need to Know about COVID-19 Caused by Coronavirus"—https://web.archive.org/web/20200805131144/https://positivehealthcare.net/covid-19/—Mar. 30, 2020).*
International Search Report issued on Jun. 15, 2021 in corresponding International Application No. PCT/CN2021/080152; 4 pages( including English translation).
Search Report issued on Jul. 16, 2021 in corresponding Chinese Application No. 202010319195.1 , 7 pages (including English translation).
Office Action issued on Jul. 21, 2021 in corresponding Chinese Application No. 202010319195.1 , 13 pages (including English translation).
Supplementary search report issued on Oct. 27, 2021 in corresponding Chinese Application No. 202010319195.1 , 1 pages.

(Continued)

*Primary Examiner* — Susan Hoffman
(74) *Attorney, Agent, or Firm* — Maier & Maier, PLLC

(57) ABSTRACT

Application of a traditional Chinese medicine composition to preparation of a medicine for treating or preventing coronavirus infection. The traditional Chinese medicine composition includes: 5-30 parts of *Herba houttuyniae*, 5-30 parts of *Flos lonicerae*, 5-20 parts of *Radix paeoniae rubra*, 3-15 parts of *Folium artemisiae argyi* and 3-15 parts of *Herba menthae*. The traditional Chinese medicine composition has a good effect of treating or preventing coronavirus-related diseases.

7 Claims, No Drawings

(56) References Cited

OTHER PUBLICATIONS

Hong et al., "A preliminary study on the prevention and treatment of influenza, SARS and human avian influenza in traditional Chinese medicine", FujianJournal of TCM, vol. 36, No. 4, Aug. 2005, 5 pages (including English translation).

Gong et al., "The Clinical Characteristics and Medication Analysis of Corona Virus Disease 2019", World Chinese Medicine vol. 15, No. 6, Mar. 2020, 8 pages (including English abstract).

Chan et al., "COVID-19 : An Update on the Epidemiological, Clinical, Preventive, and Therapeutic Evidence and Guidelines of Integrative Chinese-Western Medicine for the Management of 2019 Novel Coronavirus Disease", The American Journal of Chinese Medicine, vol. 48, No. 3, Mar. 2020, 26 pages.

* cited by examiner

APPLICATION OF TRADITIONAL CHINESE MEDICINE COMPOSITION TO PREPARATION OF MEDICINE FOR TREATING OR PREVENTING CORONAVIRUS INFECTION

TECHNICAL FIELD

The present application relates to the field of medicines for treating diseases, and in particular to application of a traditional Chinese medicine composition to preparation of a medicine for treating or preventing coronavirus infection.

BACKGROUND

On Mar. 11, 2020, the World Health Organization (WHO) officially defined COVID-19 as a global pandemic. At present, there is no effective vaccine or medicine to prevent and treat the virus, so it is particularly urgent to find effective medicines for the virus. Traditional Chinese medicine has a long history in treating plague, and has played an important role in the prevention and control of various epidemic situations. Shuangyu Granules related to the present application are refined by extracting effective ingredients from the *Herba houttuyniae*, the *Flos lonicerae*, the *Radix paeoniae rubra*, the *Folium artemisiae argyi* and the *Herba menthae* by a modern process, and can significantly improve dry throat, sore throat, swelling of throat node, thirst and fever caused by exogenous wind-heat and excessive heat of lung and stomach, acute and chronic tonsillitis, acute and chronic pharyngitis, and upper respiratory tract infection. It is urgent to carry out scientific research on whether Shuangyu Granules can effectively prevent and treat coronavirus-related diseases, especially COVID-19.

SUMMARY

In view of this, the present application aims to provide application of a traditional Chinese medicine composition to preparation of a medicine for treating or preventing coronavirus infection, where the traditional Chinese medicine composition includes the following raw materials in parts by weight: 5-30 parts of *Herba houttuyniae*, 5-30 parts of *Flos lonicerae*, 5-20 parts of *Radix paeoniae rubra*, 3-15 parts of *Folium artemisiae argyi* and 3-15 parts of *Herba menthae*.

Further, the diseases infected with coronavirus include COVID-19 (novel coronavirus pneumonia).

Further, the traditional Chinese medicine composition includes: 5-25 parts of *Herba houttuyniae*, 5-25 parts of *Flos lonicerae*, 5-15 parts of *Radix paeoniae rubra*, 3-10 parts of *Folium artemisiae argyi* and 3-10 parts of *Herba menthae*.

Further, the traditional Chinese medicine composition includes: 15-25 parts of *Herba houttuyniae*, 15-25 parts of *Flos lonicerae*, 10-15 parts of *Radix paeoniae rubra*, 5-10 parts of *Folium artemisiae argyi* and 3-5 parts of *Herba menthae*.

Optionally, the traditional Chinese medicine composition includes: 20 parts of *Herba houttuyniae*, 20 parts of *Flos lonicerae*, 12 parts of *Radix paeoniae rubra*, 8 parts of *Folium artemisiae argyi* and 4 parts of *Herba menthae*.

Optionally, the traditional Chinese medicine composition includes: 15 parts of *Herba houttuyniae*, 15 parts of *Flos lonicerae*, 12 parts of *Radix paeoniae rubra*, 7 parts of *Folium artemisiae argyi* and 7 parts of *Herba menthae*.

Optionally, the traditional Chinese medicine composition includes: 10 parts of *Herba houttuyniae*, 10 parts of *Flos lonicerae*, 8 parts of *Radix paeoniae rubra*, 4 parts of *Folium artemisiae argyi* and 4 parts of *Herba menthae*.

The composition provided by the present application may be directly ground into powder, or may be an extract prepared by a conventional method in the field. In the composition, several compositions may be directly ground into powder according to a traditional method, or extracts may be prepared by the conventional method, thereby being prepared into various dosage forms, achieving better curative effect and being more conducive to being prepared into modern medicine dosage forms.

Specifically, the medicine for treating or preventing coronavirus infection includes an oral administration dosage form, an injection administration dosage form or an external administration dosage form.

Specifically, the medicine for treating or preventing coronavirus infection includes decoction, tablet, capsule, granule, pill, injection, condensed decoction, suspending agent, dispersing agent, syrup, suppository, gel, aerosol, patch and oral liquid.

Further, a preparation method of the traditional Chinese medicine composition provided by the present application may include the following steps:

step A: weighing traditional Chinese medicine materials according to the weight proportion of the raw material medicines;

step B: extracting the *Flos lonicerae* with 50%-80% ethanol in an amount which is 6-12 times the weight of the *Flos lonicerae*, filtering the extracting solution, recovering the ethanol, drying and crushing to obtain a dry paste powder;

step C: throwing the *Herba houttuyniae*, the *Folium artemisiae argyi* and the *Herba menthae* into an extracting tank, adding water, in an amount which is 3-12 times the weight of the *Herba houttuyniae*, the *Folium artemisiae argyi* and the *Herba menthae*, extracting volatile oil, adding *Radix paeoniae rubra* crude powder into the medicine residues, adding water, in an amount which is 6-12 times the weight of the medicine residues and the *Radix paeoniae rubra* crude powder to perform decoction, filtering the extracting solution to obtain a clear paste, adding ethanol with the concentration more than 90% until the alcohol content is 60%-80%, performing alcohol precipitation, standing, recovering the ethanol from the supernatant to obtain a thick paste, and drying and crushing to obtain a dry paste powder; and step D: mixing the volatile oil and the dry paste powder.

Further, a preparation method of the traditional Chinese medicine composition provided by the present application may include the following steps:

step A: adding 50% ethanol, in an amount which is 12 times the weight of the *Flos lonicerae*, into the *Flos lonicerae*, performing reflux extraction twice, for 0.5 hour at each time, filtering, combining the filtrates, recovering the ethanol under reduced pressure (−0.07 MPa-−0.09 MPa, 65° C.-75° C.), and performing concentration to obtain a thick paste with a relative density of 1.20-1.25 (65° C.), drying under reduced pressure (−0.07 MPa-−0.09 MPa, 60° C.-65° C.) and crushing to obtain a dry extract powder of an alcohol-extracted part;

step B: adding water, in an amount which is 8 times the weight of the *Herba houttuyniae*, the *Folium artemisiae argyi* and the *Herba menthae*, into the *Herba houttuyniae*, the *Folium artemisiae argyi* and the *Herba menthae*, extracting volatile oil through steam distillation for 5 hours, filtering the extracting solution, and storing the filtrate in another container for future use;

step C: grinding and clathrating the obtained volatile for 20 minutes by using β-cyclodextrin, in an amount which is 10 times the weight of the volatile, and water, in an amount which is 20 times the weight of the volatile, drying the clathrate (55° C.), and crushing the clathrate to obtain a volatile oil clathrate; and step D: after extracting the volatile oil, combining the medicine residues and the *Radix paeoniae rubra*, adding water, in an amount which is 10 times the weight of the medicine residues and the *Radix paeoniae rubra*, performing extraction twice, for 1 hour at each time, combining the extracting solution and the oil-extracted medicine liquid (the residual medicine liquid after the volatile oil is extracted), filtering, concentrating the filtrate under reduced pressure (−0.07 MPa--0.09 MPa, 75° C.-85° C.) to obtain a clear paste with a relative density of 1.02-1.05 (70° C.), cooling to room temperature, adding 95% ethanol to make the alcohol content reach 70%, standing for more than 12 hours, performing alcohol precipitation, recovering the ethanol from the supernatant under reduced pressure (−0.07 MPa--0.09 MPa, 65° C.-75° C.), performing concentration to obtain a thick paste with a relative density of 1.25-1.30 (65° C.), optionally, adding a proper amount of dextrin, drying under reduced pressure (−0.07 MPa--0.09 MPa, 75° C.) and crushing to obtain a dry extract powder of a water-extracted part; and mixing the above three intermediates.

According to the present application, the inhibition effects of the traditional Chinese medicine composition on the coronavirus SARS-CoV-2 at different concentrations are investigated on Vero cells. The experimental results show that at the concentrations of 3000 μg/ml, 1000 μg/ml and 200 μg/ml, the traditional Chinese medicine composition has good protective effect on the Vero cells infected with the SARS-CoV-2 virus, and can inhibit the replication of the SARS-CoV-2 in cells, so that the cytopathic effect does not occur in the infected cells, indicating that the traditional Chinese medicine composition provided by the present application has a good effect of treating or preventing coronavirus-related diseases.

DETAILED DESCRIPTION OF THE EMBODIMENTS

The present application provides application of a traditional Chinese medicine composition. Those skilled in the art may learn from the contents of the specification to appropriately improve process parameters. It should be noted that all the similar substitutions and modifications are obvious to those skilled in the art and should be considered to be included in the present application. The method and application of the present application have been described by preferred embodiments, and relevant personnel obviously can modify or appropriately change and combine the method and application of the specification without departing from the content, spirit and scope of the present application to implement and apply the technology of the present application. Apparently, the described embodiments are merely some rather than all of the embodiments of the present application.

If no specific conditions are specified, the present application should be carried out according to the conventional conditions or the conditions suggested by manufacturers. The used raw material medicines or auxiliary materials, and the used agents or instruments which are not specified with the manufacturer are conventional commercially-available products. The present application is further described below with reference to embodiments.

Embodiment 1 Preparation of Traditional Chinese Medicine Composition Granules The proportion of the raw material medicines: 750 g of *Herba houttuyniae,* 750 g of *Flos lonicerae,* 450 g of *Radix paeoniae rubra,* 300 g of *Folium artemisiae argyi* and 150 g of *Herba menthae.*

Step A: 50% ethanol, in an amount which was 12 times the weight of the *Flos lonicerae,* was added into the *Flos lonicerae,* reflux extraction was performed twice, for 0.5 hour at each time, filtering was performed, the filtrates were combined, the ethanol was recovered under reduced pressure (−0.07 MPa--0.09 MPa, 65° C.-75° C.), and concentration was performed to obtain a thick paste with a relative density of 1.20-1.25 (65° C.), the thick paste was dried under reduced pressure (−0.07 MPa--0.09 MPa, 60° C.-65° C.) and crushed to obtain a dry extract powder of an alcohol-extracted part.

Step B: water, in an amount which was 8 times the weight of the *Herba houttuyniae,* the *Folium artemisiae argyi* and the *Herba menthae,* was added into the *Herba houttuyniae,* the *Folium artemisiae argyi* and the *Herba menthae,* volatile oil was extracted through steam distillation for 5 hours, and the extracting solution was filtered and stored in another container for future use.

Step C: the obtained volatile was ground and clathrated for 20 minutes by using β-cyclodextrin, in an amount which was 10 times the weight of the volatile, and water, in an amount which was 20 times the weight of the volatile, and the clathrate was dried (55° C.) and crushed to obtain a volatile oil clathrate.

Step D: after the volatile oil was extracted, the medicine residues and the *Radix paeoniae rubra* were combined, water, in an amount which was 10 times the weight of the medicine residues and the *Radix paeoniae rubra,* was added, extraction was performed twice, for 1 hour at each time, the extracting solution and the oil-extracted medicine liquid were combined and filtered, the filtrate was concentrated under reduced pressure (−0.07 MPa--0.09 MPa, 75° C.-85° C.) to obtain a clear paste with a relative density of 1.02-1.05 (70° C.) and was cooled to room temperature, 95% ethanol was added to make the alcohol content reach 70%, standing was performed for more than 12 hours, alcohol precipitation was performed, the ethanol was recovered from the supernatant under reduced pressure (−0.07 MPa--0.09 MPa, 65° C.-75° C.) and concentrated to obtain a thick paste with a relative density of 1.25-1.30 (65° C.), a proper amount of dextrin was added, drying was performed under reduced pressure (−0.07 MPa--0.09 MPa, 75° C.) and crushing was performed to obtain a dry extract powder of a water-extracted part. The above three intermediates and a proper amount of dextrin and steviosin were mixed uniformly, and dry granulation was performed to prepare 1000 g of granules.

Embodiment 2 Preparation of Traditional Chinese Medicine Buccal Tablets

The proportion of the raw material medicines: 560 g of *Herba houttuyniae,* 560 g of *Flos lonicerae,* 450 g of *Radix paeoniae rubra,* 275 g of *Folium artemisiae argyi* and 275 g of *Herba menthae.*

Step A: traditional Chinese medicine materials were weighed according to the weight proportion of the raw material medicines, the *Flos lonicerae* was cleaned, the *Radix paeoniae rubra* was coarsely crushed, the whole *Herba menthae* was crushed, and the *Herba houttuyniae* and the *Folium artemisiae argyi* were directly for future use.

Step B: the *Flos lonicerae* was subjected by reflux extraction by using 50% ethanol, in an amount which was 12 times the weight of the *Flos lonicerae*, twice, for 0.5 hour at each time, the extracting solutions were combined and filtered, the ethanol was recovered to obtain an extract 1 with the proportion of 1.20-1.30 (60-80° C.), and drying was performed to obtain a dry paste powder 1 for future use.

Step C: water, in an amount which was 8 times the weight of the *Herba houttuyniae*, the *Folium artemisiae argyi* and the *Herba menthae*, was added and heated to 80° C., the *Herba houttuyniae*, the *Folium artemisiae argyi* and the *Herba menthae* were sequentially added, volatile oil was extracted continuously for 5 hours to obtain the volatile oil, water, in an amount which was 10 times the weight of the medicine residues and the *Radix paeoniae rubra*, was added into the medicine residues and the *Radix paeoniae rubra*, decoction was performed twice, for 1 hour at each time, the extracting solutions were combined, filtered and concentrated to obtain a clear paste with a relative density of 1.02-1.05 (60° C.), adding 95% ethanol until the alcohol content is 70%, alcohol precipitation was performed, standing was performed for 12-32 hours, the ethanol was recovered from the supernatant to obtain a thick paste 2 with a relative density of 1.20-1.30 (60° C.), and the thick paste 2 was dried and crushed to obtain a dry paste powder 2 for future use.

Step D: the obtained volatile oil was clathrated by a colloid mill through grinding to obtain a volatile oil clathrate 3, and the volatile oil clathrate 3 was crushed for future use. The dry paste powder 1, the dry paste powder 2, the clathrate 3 and auxiliary material commonly used for the buccal tablets were mixed uniformly, and granulation, sieving, tabletting and internal packaging were performed.

Embodiment 3 Preparation of Traditional Chinese Medicine Composition Spray

The proportion of the raw material medicines: 350 g of *Herba houttuyniae,* 350 g of *Flos lonicerae,* 280 g of *Radix paeoniae rubra,* 150 g of *Folium artemisiae argyi* and 150 g of *Herba menthae.*

Step A: traditional Chinese medicine materials were weighed according to the weight proportion of the raw material medicines, the *Flos lonicerae* was cleaned, the *Radix paeoniae rubra* was coarsely crushed, the whole *Herba menthae* was crushed, and the *Herba houttuyniae* and the *Folium artemisiae argyi* were directly for future use.

Step B: the *Flos lonicerae* was subjected by reflux extraction by using 50% ethanol, in an amount which was 12 times the weight of the *Flos lonicerae*, twice, for 0.5 hour at each time, the extracting solutions were combined and filtered, the ethanol was recovered to obtain an extract 1 with the proportion of 1.20-1.30 (60-80° C.), and concentration was performed to obtain thick paste 1 for future use.

Step C: water, in an amount which was 8 times the weight of the *Herba houttuyniae*, the *Folium artemisiae argyi* and the *Herba menthae*, was added and heated to 80° C., the *Herba houttuyniae*, the *Folium artemisiae argyi* and the *Herba menthae* were sequentially added, volatile oil was extracted continuously for 5 hours, water, in an amount which was 10 times the weight of the medicine residues and the *Radix paeoniae rubra*, was added into the medicine residues and the *Radix paeoniae rubra*, decoction was performed twice, for 1 hour at each time, the extracting solutions were combined, filtered and concentrated to obtain a clear paste with a relative density of 1.02-1.05 (60° C.), 95% ethanol was added until the alcohol content was 70%, alcohol precipitation was performed, standing was performed for 12-32 hours, the ethanol was recovered from the supernatant to obtain a thick paste 2 with a relative density of 1.20-1.30 (60° C.) for future use.

Step D: the thick paste 1 and the thick paste 2 were mixed uniformly, the volatile oil was added by using auxiliary materials commonly used for preparation of the spray, the materials were mixed uniformly and packaged in a pressure-resistant container with a special valve system.

Embodiment 4 Inhibition Effect of Traditional Chinese Medicine on SARS-CoV-2

1. Experimental Materials

Test medicine: medicine prepared in Embodiment 1 of the present application.

Cell: Vero cell, preserved in Cell Bank of Institute of Microbiological Epidemiology.

Virus: SARS-CoV-2, having a titer of $10^7$ $CCID_{50}$/ml, and preserved in Virus Reservoir of Institute of Microbiological Epidemiology and P3 virus seed refrigerator at −80° C. The virus titer was 100 $CCID_{50}$/well.

2. Experimental Method

100 µl of Vero cells with the concentration of $1 \times 10^5$ cell/ml was added into each well of a sterile 96-well culture plate, and cultivation was performed under the conditions of 37° C. and 5% $CO_2$ for 24 hours; the test medicine was diluted into three concentrations such as 3000 µg(preparation)/ml, 1000 µg(preparation)/ml and 200 µg(preparation)/ml, 3 duplicate-wells were set for each concentration, 100 µl was in each well to act for 1 hour, and then the isovolumetric 100 $CCID_{50}$ virus was added in each well to act for 1 hour; after 1 hour, all the liquid in the 96-well culture plate was discarded, and the diluted medicine liquid was added; meanwhile, cell control, blank control (solvent control) and virus control (negative control) were set; cells were incubated in an incubator under the conditions of 37° C. and 5% $CO_2$ for 5 days; cytopathic effect (CPE) was observed under an optical microscope, and the cytopathic effect degree of the cells were record according to the 5-level standard: complete cytopathic effect of the cells was recorded as "++++", 75% cytopathic effect was recorded as "+++", 50% cytopathic effect was recorded as "++", 25% cytopathic effect was recorded as "+", and non-cytopathic effect was recorded as "−".

3. Experiment condition: all the experimental operations were completed in BSL-3 laboratory.

4. Result judgment: the cell without CPE has the effective concentration for inhibiting virus, and the cell with CPE has the non-effective concentration.

5. Experimental Results:

At the three concentrations of the medicine group according to the present application, there is no cytopathic effect, and the results are shown Table 1.

TABLE 1

| Anti-SARS-CoV-2 (CPE) of the medicine | | |
|---|---|---|
| Name of Test Medicine | Concentration (μg/ml) | Result |
| Medicines of the present application | 3000 | − |
| | 1000 | − |
| | 200 | − |
| Virus control | / | ++++ |
| Cell control | / | − |

Notes:
"−" means no cytopathic effect; and "++++" means complete cytopathic effect.

6. Conclusion:

According to the screening results of cell level, the samples prepared according to Embodiment 1 of the present application can inhibit the replication of SARS-CoV-2 in the cells at three concentrations of 3000 μg/ml, 1000 μg/ml and 200 μg/ml, indicating that the medicine provided by the present application has good anti-SARS-CoV-2 activity in vitro.

It should be noted that those skilled in the art may learn from the contents of the specification to appropriately improve process parameters, and all the similar substitutions and modifications are obvious to those skilled in the art and should be considered to be included in the present application.

What is claimed is:

1. A method of using a medicine composition to treat COVID-19 coronavirus infection, the medicine composition comprising: 5-30 parts of *Herba houttuyniae,* 5-30 parts of *Flos lonicerae,* 5-20 parts of *Radix paeoniae rubra,* 3-15 parts of *Folium artemisiae argyi* and 3-15 parts of *Herba menthae.*

2. The method according to claim 1, wherein the medicine composition comprises: 5-25 parts of *Herba houttuyniae,* 5-25 parts of *Flos lonicerae,* 5-15 parts of *Radix paeoniae rubra,* 3-10 parts of *Folium artemisiae argyi* and 3-10 parts of *Herba menthae.*

3. The method according to claim 1, wherein the medicine composition comprises: 15-25 parts of *Herba houttuyniae,* 15-25 parts of *Flos lonicerae,* 10-15 parts of *Radix paeoniae rubra,* 5-10 parts of *Folium artemisiae argyi* and 3-5 parts of *Herba menthae.*

4. The method according to claim 1, wherein the medicine composition comprises: 15 parts of *Herba houttuyniae,* 15 parts of *Flos lonicerae,* 12 parts of *Radix paeoniae rubra,* 7 parts of *Folium artemisiae argyi* and 7 parts of *Herba menthae.*

5. The method according to claim 1, wherein the medicine composition comprises: 20 parts of *Herba houttuyniae,* 20 parts of *Flos lonicerae,* 12 parts of *Radix paeoniae rubra,* 8 parts of *Folium artemisiae argyi* and 4 parts of *Herba menthae.*

6. The method according to claim 1, wherein the medicine for treating coronavirus infection comprises an oral administration dosage form, an injection administration dosage form or an external administration dosage form.

7. The method according to claim 6, wherein the medicine for treating coronavirus infection comprises decoction, tablet, capsule, granule, pill, injection, condensed decoction, suspending agent, dispersing agent, syrup, suppository, gel, aerosol, patch and oral liquid.

* * * * *